US012698310B2

(12) United States Patent
Newton

(10) Patent No.: US 12,698,310 B2
(45) Date of Patent: Aug. 4, 2026

(54) COMPOSITIONS AND METHODS FOR INSECT CONTROL

(71) Applicant: Indiana University Research and Technology Corporation, Indianapolis, IN (US)

(72) Inventor: Irene Newton, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 906 days.

(21) Appl. No.: 17/375,764

(22) Filed: Jul. 14, 2021

(65) Prior Publication Data

US 2023/0022700 A1 Jan. 26, 2023

Related U.S. Application Data

(62) Division of application No. 16/094,178, filed as application No. PCT/US2017/028957 on Apr. 21, 2017, now abandoned.

(60) Provisional application No. 62/325,923, filed on Apr. 21, 2016.

(51) Int. Cl.
*C07K 14/195* (2006.01)
*C07K 14/435* (2006.01)
*C12N 15/113* (2010.01)
*C12N 15/62* (2006.01)
*C12N 15/85* (2006.01)

(52) U.S. Cl.
CPC ...... *C07K 14/195* (2013.01); *C07K 14/43563* (2013.01); *C12N 15/113* (2013.01); *C12N 15/62* (2013.01); *C12N 15/85* (2013.01); *C12N 2310/20* (2017.05); *C12N 2800/105* (2013.01); *C12N 2800/22* (2013.01); *C12N 2830/75* (2013.01)

(58) Field of Classification Search
CPC .................................................. C07K 14/195
See application file for complete search history.

(56) References Cited

U.S. PATENT DOCUMENTS 9,125,388 B2 * 9/2015 Alphey .............. C12N 15/8238
2014/0056938 A1 2/2014 Weaver et al.
2019/0127425 A1 5/2019 Newton

OTHER PUBLICATIONS

Martin et al., 2024, PLoS Pathogens, vol. 20(3), pp. 1-22 (Year: 2024).*
Munikrishnappa et al. (2014, Asian Pac. J. Trop. Dis., vol. 4(1), pp. 78-81) (Year: 2014).*
Newton et al. (Abstract, 8th Int. Wolbachia Conference, 2014, Innsbruck, Austria) (Year: 2014).*
Wu et al., 2004, PLoS Biology, vol. 2(3), pp. 327-341) (Year: 2004).*
GenBank accession No. AE017196.1, Jan. 31, 2014. (Year: 2014).*
Miller et al. Stable Integration and Expression of a Bacterial Gene in the Mosquito Anopheles gambiae, Science, vol. 237:779-781, dated Aug. 14, 1987, 3 pages.
GenBank Accession 14517.1. Hypothetic protein WD_0830 (Wolbachia endosymbiont of *Drosophila melanogaster*), published Jan. 31, 2014 and available online: https:www.ncbi.nim.nih.gov/protein/42410408; 2 pages.
International Preliminary Report on Patentability received for PCT Patent Application No. PCT/US2017/028957, mailed on Nov. 1, 2018, 8 pages.
International Search Report and Written Opinion issued by the ISA/US, Commissioner for Patents, mailed Sep. 8, 2017, for International Application No. PCTUS2017028957; 11 pages.
Newton et . "Necessity is the mother of invention: actin manipulations by the reproductive parasite Wolbachia pipientis" published Jun. 11, 2014 as an abstract in 8th International Wolbachia Conference, Abstract Book kpg 36 and available online: https:www.oegef.at/downloads/WOLBACHIA_2014_Abstacts.pdf.

* cited by examiner

*Primary Examiner* — Anoop K Singh
*Assistant Examiner* — David A Montanari
(74) *Attorney, Agent, or Firm* — Faegre Drinker Biddle & Reath LLP

(57) ABSTRACT

Described herein are expression vectors encoding the *Wolbachia* protein WalE1. Also described are insects transformed with an expression vector of the present disclosure, and progeny thereof. Also described are methods for improving *Wolbachia* replication and transmission in its insect host by overexpressing WalE1 in the insect host. Improved *Wolbachia* replication and transmission provides for insect population control and pathogen resistance in insects, which can reduce disease transmission.

10 Claims, 10 Drawing Sheets

Specification includes a Sequence Listing.

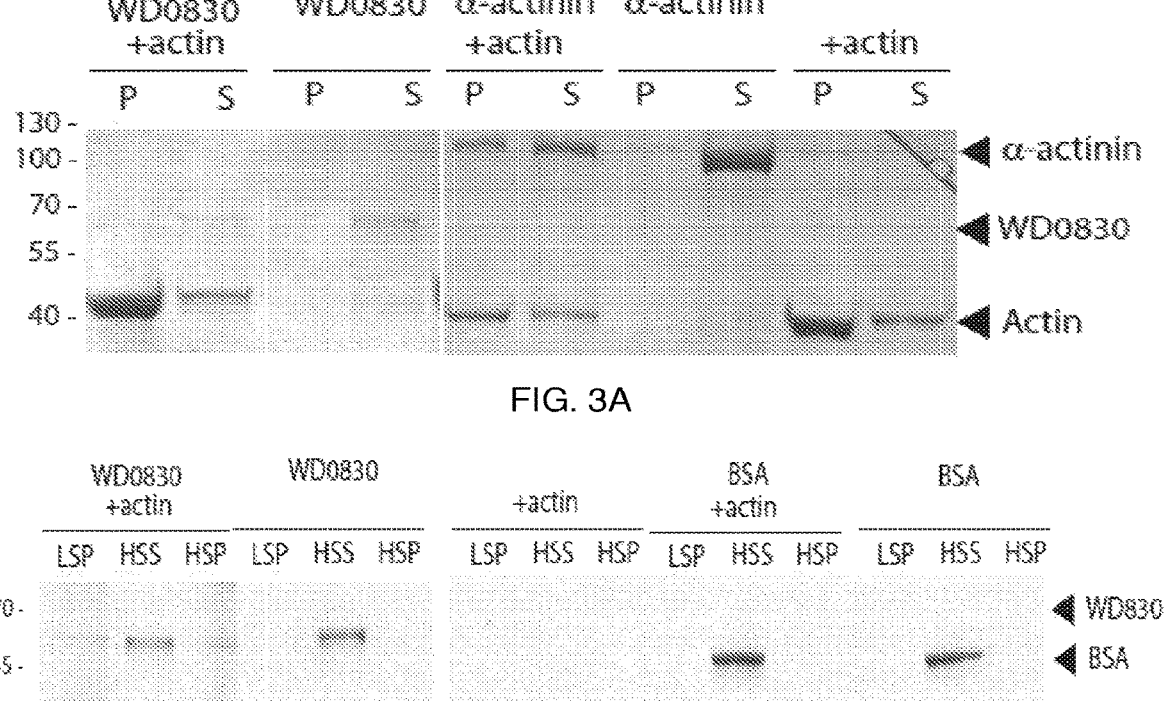
FIG. 3A
FIG. 3B
FIG. 3C

Control
w-;osk-Gal4/+;+

Experimental
w-;osk-Gal4/+;P{UASp-RFP.WalE1}6M/+

COMPOSITIONS AND METHODS FOR INSECT CONTROL

CROSS-REFERENCE TO RELATED APPLICATIONS

This application is a divisional of U.S. patent application Ser. No. 16/094,178, filed on Oct. 16, 2018, which is a U.S. national stage entry of International PCT Application No. PCT/US2017/028957, filed Apr. 21, 2017, which claims priority to U.S. Provisional Application No. 62/325,923, which was filed on Apr. 21, 2016, the entire disclosures of which are expressly incorporated herein by reference for all purposes.

STATEMENT REGARDING FEDERALLY SPONSORED RESEARCH

This invention was made with government support under grant no. 1456545 awarded by the National Science Foundation. The Government has certain rights in the invention.

SEQUENCE LISTING

A Sequence Listing containing SEQ ID NOs: 1-22 is hereby incorporated by reference in its entirety.

BACKGROUND

*Wolbachia pipientis* is a ubiquitous alpha-proteobacterium related to the Rickettsial pathogens *Ehrlichia* and *Anaplasma* that infects arthropods and nematodes. *Wolbachia pipientis*, which infects approximately 40% of insect species, is passed from generation to generation both vertically (through the oocyte) and horizontally (by environmental transmission).

*Wolbachia pipientis* causes a persistent infection within insects, often inducing reproductive effects including sperm-egg incompatibility (cytoplasmic incompatibility), male-killing, and feminization. Due to the induced cytoplasmic incompatibility effect, production of unviable progeny occurs when an uninfected male mates with a *Wolbachia*-infected female. The endosymbiotic bacteria rapidly invade and spread within the host population. Certain strains of *Wolbachia* also have life-shortening effects in the host.

In addition to its effects on fertility and life-span, *Wolbachia* has also been observed to protect insect hosts from RNA virus infection by inhibiting replication (e.g., dengue virus, Chikungunya virus, and yellow fever virus). For example, the introduction of wMel and wMelPop-CLA strains of *Wolbachia* into the mosquito *Aedes aegypti*, the main vector of dengue virus, resulted in the generation of insects that do not support replication of the virus, thus inhibiting its transmission.

SUMMARY

The following embodiments and aspects thereof are described and illustrated in conjunction with systems, tools and methods that are meant to be illustrative, not limiting in scope. In various embodiments, one or more of the above-described problems have been reduced or eliminated, while other embodiments are directed to other improvements.

The present disclosure provides expression vectors encoding the *Wolbachia* protein WalE1 and functional fragments thereof, insects transformed with an expression vector of the present disclosure and progeny thereof, and methods for enhancing *Wolbachia* replication and transmission in its insect host by overexpressing WalE1 in the insect host. Enhanced *Wolbachia* replication and transmission results in insect population control and enhanced pathogen resistance in insects, which can both reduce disease transmission.

In one aspect, provided herein is an expression vector, comprising a polynucleotide that encodes WalE1 (WD0830) or a functional fragment of WalE1 (WD0830). In some embodiments, the polynucleotide is operably linked to an expression control sequence. In some embodiments, the polynucleotide is codon optimized for expression in a particular host. The expression vector can be expressible in an insect, such as *Aedes albopictus*, *Aedes aegypti*, *Anopheles gamibiae*, *Anopheles stephansi*, *Culex pipiens*, *Culex tarsalis*, *Culex quinquefasciatus*, an insect of the Culicidae family, or an insect of the Drosophilidae family. In some embodiments, the insect is a disease vector, such as a mosquito.

In some embodiments, functional fragments of WalE1 are those that have a synuclein domain. In some embodiment, the synuclein domain is an alpha-synuclein domain.

In another aspect, provided herein is an insect transformed with an expression vector of the present disclosure. Also provided are progeny of the transformed insect. In some embodiments, the transformed insect or progeny thereof overexpress WalE1 or a functional fragment of WalE1, where the overexpressing is relative to an insect that has not been transformed with the expression vector.

In another aspect provided herein is a method for increasing *Wolbachia* replication and transmission in an insect host population. In some embodiments, the method comprises the steps of overexpressing WalE1 or a functional fragment thereof in at least one insect, and introducing the insect overexpressing WalE1 or the functional fragment thereof, or a progeny thereof, to an insect population. Overexpression of WalE1 or a functional fragment of WalE1 can be achieved by transforming at least one insect host or insect host cell with an expression vector described herein. Through vertical inheritance, progeny of the transformed insect will also overexpress WalE1.

In some embodiments, the transformed insect is already infected by *Wolbachia*. In other embodiments, the insect is both transformed with an expression vector described herein and inoculated with *Wolbachia*.

The overexpression of WalE1 or a functional fragment thereof increases *Wolbachia* replication and transmission in the transgenic insect. Such control can reduce the risk of disease transmission from disease vectors such as mosquitos. Further, as *Wolbachia* can confer or enhance pathogen resistance in certain insects, such as mosquitos, the methods herein also provide for conferring or enhancing pathogen resistance in an insect. In certain aspects, the pathogens are viruses, protozoans, or worms.

In another aspect provided herein is a CRISPR-on system comprising dCas9 fused with a transcriptional activation domain and a single guide RNA (sgRNA) having a complementary nucleic acid sequence to a WalE1 (WD0830) expression control element.

In another aspect provided herein is a kit that has at least one container and the expression vector described herein. Kits can also include at least one live insect or insect embryo. In certain aspects, the live insect or insect embryo is infected with *Wolbachia*.

In addition to the aspects and embodiments described above, further aspects and embodiments will become apparent by reference to the drawings and by study of the following descriptions.

BRIEF DESCRIPTION OF THE DRAWINGS

Certain embodiments are illustrated in the referenced figures of the drawings. It is intended that the embodiments and figures disclosed herein are to be considered illustrative rather than limiting.

FIG. 3A is an image of two gels. Purified WD0830 and alpha-actinin (positive control actin binding protein) were incubated with polymerized rabbit skeletal actin and subjected to centrifugation at 150K×g, fractionated by SDSPAGE, and silver stained to visualize proteins in the supernatant (S) and the pellet (P).

FIG. 3B is an image of two gels. To identify actin bundling activity, polymerized rabbit skeletal actin was incubated with or without WD0830 as well as with or without bovine serum albumin (BSA, as a negative control) and subjected to a low speed (14K×g) centrifugation before high speed (150K×g) centrifugation. LSP: low speed pellet. HSS: high speed supernatant. HSP: high speed pellet.

FIG. 3C is a series of representative images visualizing actin bundling. Polymerized rabbit skeletal actin was incubated with either WD0830 or BSA then directly stained with Acti-stain 555, mounted on a slide and visualized by fluorescence microscopy (scale bar=100 μm; all images taken at the same magnification).

DETAILED DESCRIPTION

In the following sections, various exemplary compositions and methods are described in order to detail various embodiments. It will be evident to one skilled in the art that practicing the various embodiments does not require the employment of all of the specific details outlined herein, but rather that vector backbone, protein fragment composition and other specific details may be modified through experimentation. In some embodiments, well known methods or components have not been included in the description.

Figure 1A:
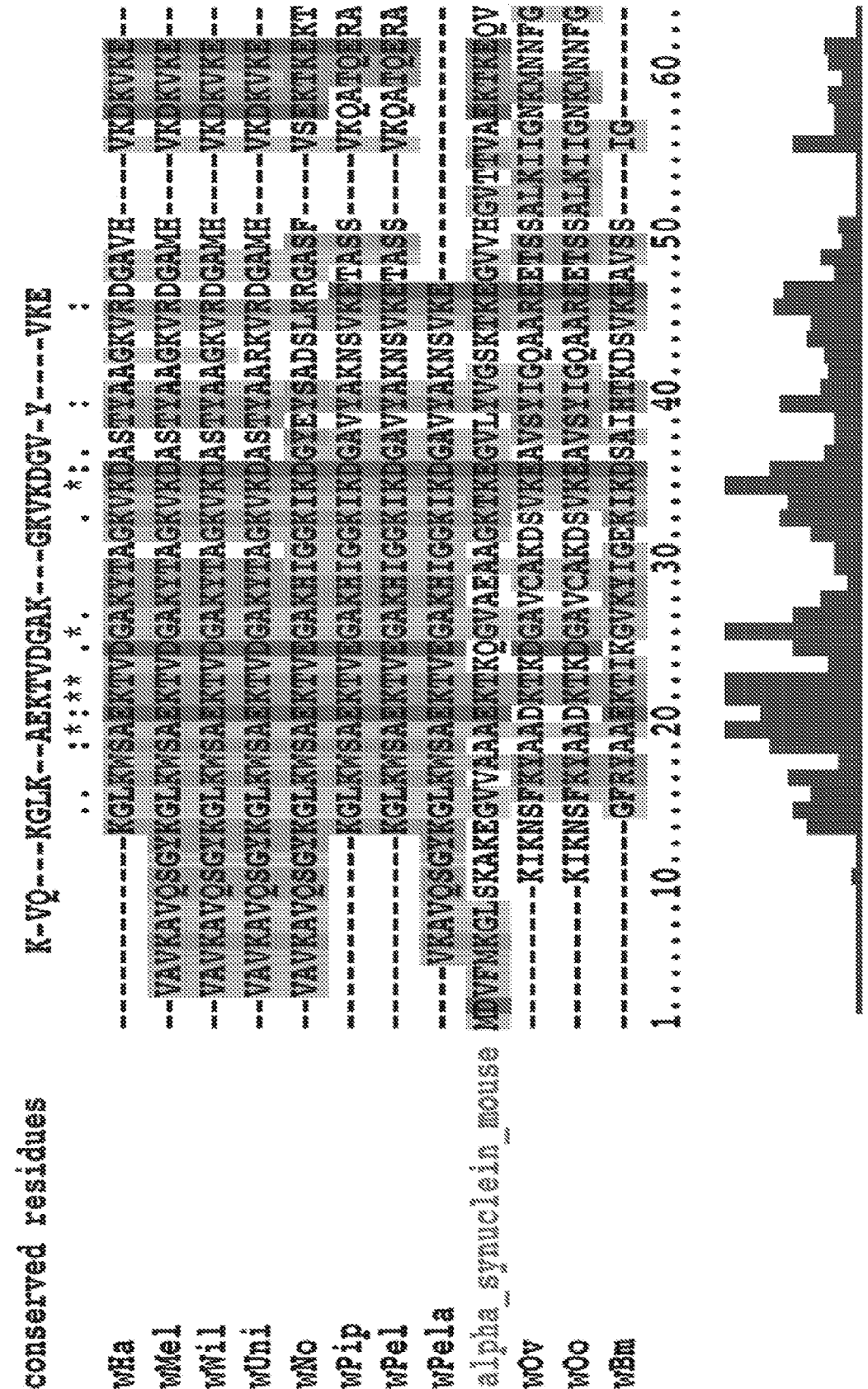
FIG. 1A depicts an alignment of the synuclein domain from WD0830 (WalE1) and *Wolbachia* homologs compared to mammalian alpha synuclein (mouse). Conserved residues are indicated at the top of the alignment. The sequences correspond to SEQ ID NOs: 3-14, in order of appearance.
Figures 1B, 1C:
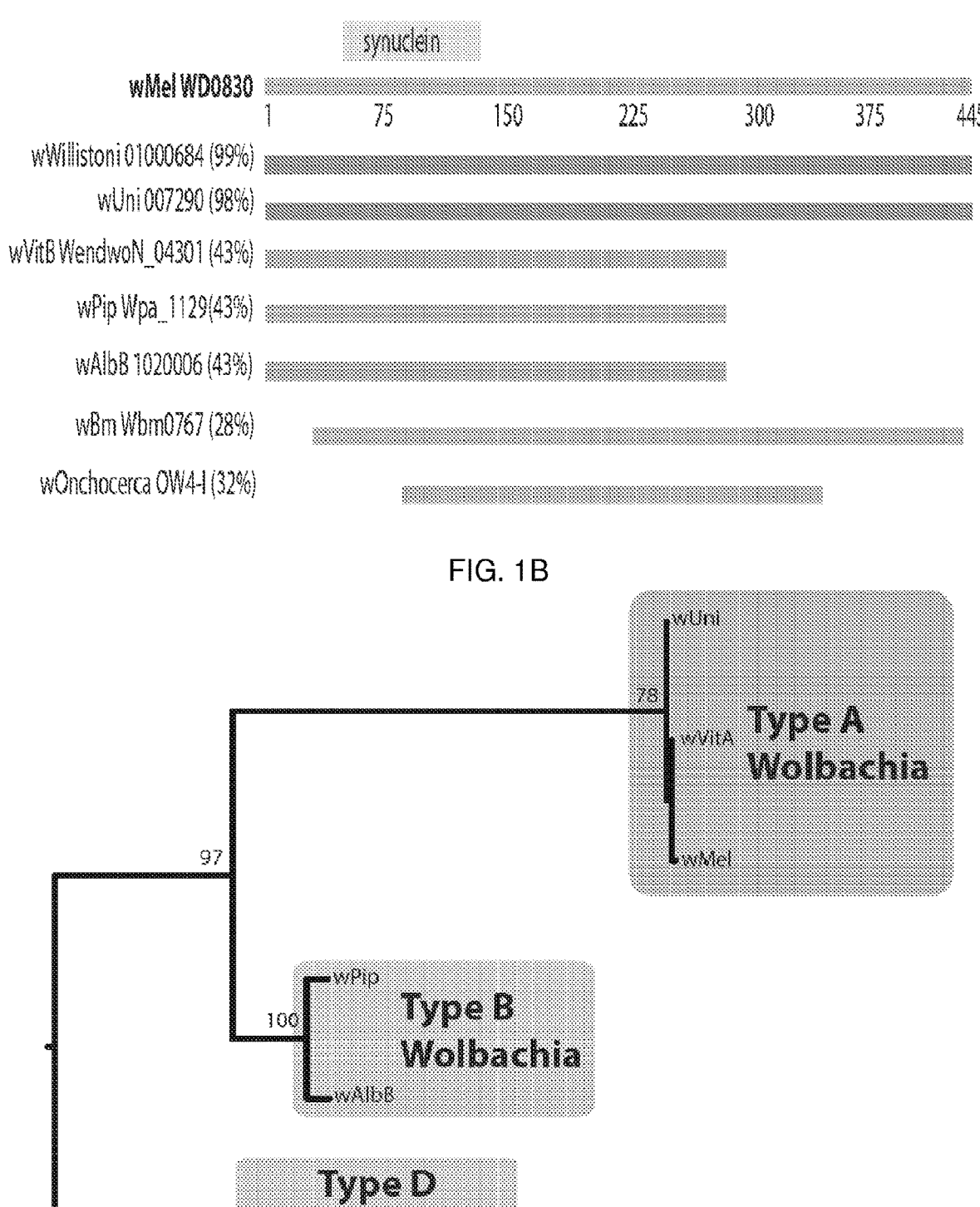
FIG. 1B illustrates the conservation (percent protein identity) and length of the WD0830 homolog across the *Wolbachia* genus. Area and percent of similarity is indicated by the colored line across the WD0830 open reading frame.
FIG. 1C depicts the phylogeny of the various open reading frames generated from codon alignment (clustalw) edited by eye and then used as input to RAxML (GTR+GAMMA), which recovers major *Wolbachia* clades.

The present disclosure and accompanying Examples describe the identification and characterization of *Wolbachia* effector protein WD0830, which has been termed *Wolbachia* actin localizing effector 1 (WalE1). As illustrated by FIGS. 1A-1C, WalE1 is a well conserved *Wolbachia* protein having a synuclein domain, a eukaryotic domain known to interact with actin. Alpha-synuclein, the mammalian homolog, colocalizes with actin filaments in vivo, and in quantitative proteomics assays, has been observed to interact with components of the cytoskeleton (such as cofilin and destrin).

Important to *Wolbachia*'s ability to induce reproductive effects in generation after generation is its ability to persist within and be passaged through the host germ line.

Figures 2A, 2B:
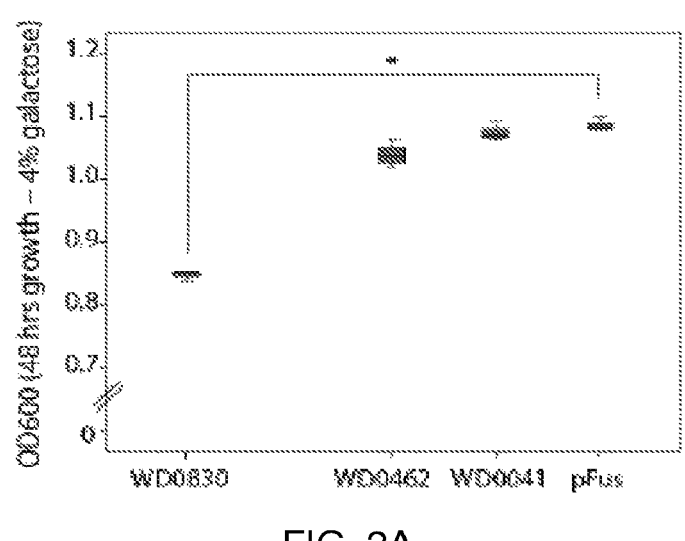
FIG. 2A is a box plot representative of yeast carrying plasmids that conditionally express GFP (pFus), GFP-WD0830, or two other *Wolbachia* proteins (WD0462 and WD0041) grown for 48 hours under inducing (4% galactose) conditions (mean of 3 replicate experiments) **=p<0.001 (t-test comparing final optical density (OD) achieved by strains expressing GFP-WD0830 to GFP alone).
FIG. 2B is a series of representative images of yeast expressing GFP-WD0830 or GFP alone and stained with rhodaminelabelled phalloidin. Arrowheads point to cortical actin punctae in control yeast (GFP only) and actin filaments in GFP-WD0830 expressing yeast.

As depicted in FIGS. 2A-2B, WalE1 ectopically expressed in yeast localizes to and manipulates the yeast actin cytoskeleton, resulting in growth inhibition. Further, WalE1 binds to and bundles filamentous (F) actin in cosedimentation assays (see FIGS. 3A-3C). In female transgenic flies harboring *Wolbachia* and overexpressing WalE1, the *Wolbachia* protein localizes to developing oocytes. In these same flies, *Wolbachia* accumulates to higher titer than genetic controls, with *Wolbachia* localizing more strongly to the developing oocyte. This effect spans generations, as offspring from these transgenic lines lay eggs with increased *Wolbachia* titers compared to controls. As described and demonstrated in the description and accompanying Examples presented herein, WalE1 functions to manipulate actin during host development and facilitate *Wolbachia* replication and transmission.

In various aspects, the present disclosure provides new materials and methods for overexpressing WalE1 in *Wolbachia*-infected hosts. WalE1, as described for the first time in the present disclosure and accompanying Examples, is a *Wolbachia* secreted effector protein that facilitates *Wolbachia* bacterial replication and transmission in an insect or nematode. In some embodiments, overexpression of WalE1 is achieved by transforming an insect or nematode host or host cell with a transgene vector and expressing the transgene vector in the insect or nematode. In some embodiments, the transgene vector comprises a transgene polynucleotide that encodes the WalE1 protein or a functional fragment of the WalE1 protein. The vector can comprise a polynucleotide that encodes a WalE1 protein, or a functional fragment of the WalE1 protein, of any *Wolbachia* species or strain. In some embodiments, the *Wolbachia* species is *Wolbachia pipientis*. In some embodiments, the *Wolbachia* strain is, wHa, wMel, wWil, wUni, wNo, wPip, wPel, wPela, wOv, wOo, wBm, wMelPop, wMelPop-CLA, wMelCS, wAu, wRi, wMau, or wCer2, although additional *Wolbachia* strains can be used, and are contemplated herein.

In one embodiment the vector comprises a polynucleotide that encodes a polypeptide having an amino acid sequence that is at least 90% identical to the amino acid sequence of wMel WalE1 protein (SEQ ID NO: 2). In other embodiments, the vector comprises a polynucleotide that encodes a polypeptide having an amino acid sequence that is from about 90% identical to 100% identical to the amino acid sequence of wMel WalE1 protein (SEQ ID NO: 2). In another embodiment, the vector comprises a polynucleotide that encodes a polypeptide having the sequence of SEQ ID NO: 2.

In some embodiments, a functional fragment of WalE1 is a protein fragment that has a synuclein domain. In other embodiments, a functional fragment of WalE1 is a protein fragment that has an alpha-synuclein domain. In yet other embodiments, the functional fragment of WalE1 comprises a polypeptide having an amino acid sequence that is at least 90% identical to any one of SEQ ID NOs: 3-10 or 12-14. In some embodiments, the functional fragment of WalE1 comprises a polypeptide having the sequence of any one of SEQ ID NOs: 3-10 or 12-14.

In some embodiments vector is in the form of a plasmid, a viral particle, a phage, and the like. In some embodiments, the vector is an expression vector. The expression vector can be, for example, an episomal expression vector, an integrative expression vector, or a viral expression vector. In some embodiments, the structural polynucleotide sequence encoding the WalE1 protein or protein fragment is inserted into the expression vector. Methods and procedures for inserting the polynucleotide sequence into the expression vector are known in the art.

A "vector" or "recombinant vector" is a nucleic acid molecule that is used as a tool for manipulating a nucleic acid sequence of choice or for introducing such a nucleic acid sequence into a host cell. A vector may be suitable for use in cloning, sequencing, or otherwise manipulating one or more nucleic acid sequences of choice, such as by expressing or delivering the nucleic acid sequence(s) of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

A vector can be either RNA or DNA, either prokaryotic or eukaryotic, and typically is a plasmid. The vector can be maintained as an extrachromosomal element (e.g., a plasmid) or it can be integrated into the chromosome of a recombinant host cell. The entire vector can remain in place within a host cell, or under certain conditions, the plasmid DNA can be deleted, leaving behind the nucleic acid molecule of choice. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector can contain at least one selectable marker.

The term "expression vector" refers to a recombinant vector that is capable of directing the expression of a nucleic acid sequence that has been cloned into it after insertion into a host cell or other (e.g., cell-free) expression system. A nucleic acid sequence is "expressed" when it is transcribed to yield an mRNA sequence. In most cases, this transcript will be translated to yield an amino acid sequence. The cloned gene is usually placed under the control of (i.e., operably linked to) an expression control sequence.

Vectors and expression vectors may contain one or more regulatory sequences or expression control sequences. Regulatory sequences broadly encompass expression control sequences (e.g., transcription control sequences or translation control sequences), as well as sequences that allow for vector replication in a host cell. Transcription control sequences are sequences that control the initiation, elongation, or termination of transcription. Suitable regulatory sequences include any sequence that can function in a host cell or organism into which the recombinant nucleic acid molecule is to be introduced, including those that control transcription initiation, such as promoter, enhancer, terminator, operator and repressor sequences. Additional regulatory sequences include translation regulatory sequences, origins of replication, and other regulatory sequences that are compatible with the recombinant cell. The expression vectors may contain elements that allow for constitutive expression or inducible expression of the protein or proteins of interest. Numerous inducible and constitutive expression systems are known in the art In some embodiments, the polynucleotide sequence of the expression vector that encodes the WalE1 protein or functional fragment thereof is operably linked to at least one expression control sequence. As used herein, the term "operably linked" refers to the association of two or more polynucleotide fragments so that the function of one is affected by the other. The term "expression control sequence," as used herein, refers to a polynucleotide having a particular sequence that regulates the expression of a polynucleotide to which it is operatively linked. Expression control sequences can control the transcription, post-transcriptional events, and translation of polynucleotide sequences. Suitable expression control sequences include constitutive promoters and inducible promoters. Appropriate promoters can be selected based on the particular vector backbone being used. Vector backbones generally possess a promoter upstream of the insertion site. It should be understood that the design of the expression vector may depend on such factors as the choice of the host cell to be transformed and/or the type of polypeptide to be expressed.

Expression and recombinant vectors may contain a selectable marker, a gene encoding a protein necessary for survival or growth of a host cell transformed with the vector. The presence of this gene allows growth of only those host cells that express the vector when grown in the appropriate selective media. Typical selection genes encode proteins that confer resistance to antibiotics or other toxic substances, complement auxotrophic deficiencies, or supply critical nutrients not available from a particular media. Markers may be an inducible or non-inducible gene and will generally allow for positive selection. Non-limiting examples of selectable markers include the ampicillin resistance marker (i.e., beta-lactamase), tetracycline resistance marker, neomycin/kanamycin resistance marker (i.e., neomycin phosphotransferase), dihydrofolate reductase, glutamine synthetase, and the like. The choice of the proper selectable marker will depend on the host cell, and appropriate markers for different hosts as understood by those of skill in the art.

Suitable expression vectors may include (or may be derived from) plasmid vectors that are well known in the art, such as those commonly available from commercial sources. Vectors can contain one or more replication and inheritance systems for cloning or expression, one or more markers for selection in the host, and one or more expression cassettes. The inserted coding sequences can be synthesized by standard methods, isolated from natural sources, or prepared as hybrids. Ligation of the coding sequences to transcriptional regulatory elements or to other amino acid encoding sequences can be carried out using established methods. A large number of vectors, including bacterial, yeast, and mammalian vectors, have been described for replication and/or expression in various host cells or cell-free systems, and may be used with the sequences described herein for simple cloning or protein expression In some embodiments, the polynucleotide encoding the WalE1 protein or functional fragment thereof is codon optimized. Any of the polynucleotides described herein can be utilized in a codon optimized form. In some embodiments, a polynucleotide is codon optimized for use in a selected host insect or nematode. Codon optimization can improve WalE1 protein or functional protein fragment expression in the host by increasing the translational efficiency of the polynucleotide that encodes the WalE1 protein or functional protein fragment. Codon optimization can be performed with the assistance of publicly available software, such as Gene Designer (DNA 2.0). In some embodiments, additional modifications to the encoding polynucleotide are performed to minimize unwanted restriction sites, internal ribosomal binding site sequences, and other sequences such as internal termination sequences and repeat sequences. These codon-optimization methods have been demonstrated to result in up to approximately 1000 fold higher expression of heterologous genes in target organisms (see, e.g., Welch et al., PLoS One 4, e7002; 2009 and Welch et al., Journal of the Royal Society; Interface 6 (Suppl 4), S467-S476; 2009). Accordingly, in some embodiments, the polynucleotide sequences encoding WalE1, or a fragment thereof, are modified so that they will have improved expression in a target host.

In some embodiments, the transgene vector encoding WalE1, or a fragment thereof, is expressible in an insect. The term "expressible in an insect," as used herein, describes the ability of the transgene vector, such as an expression vector, to express the transgene in the host insect. For example, in some embodiments, the vectors described herein are readily expressed in a target host insect, resulting in the overexpression of WalE1 or a functional fragment thereof relative to a target host insect harboring *Wolbachia* but lacking the vector.

Insect target hosts include, but are not limited to, insects of the Culicidae and Drosophilidae families. A particular target host is *Drosophila melanogaster*. Other target hosts include disease vectors, including but not limited to Asian tiger mosquito (*Aedes albopictus*) and yellow fever mosquito (*Aedes aegypti*), which can also transmit mosquito-borne viruses such as dengue and West-Nile; malaria mosquitoes (*Anopheles* gamibiae, *Anopheles* stephansi); and other species, such as *Culex pipiens, Culex tarsalis*, and *Culex quinquefasciatus*, which are all known West-Nile virus mosquito vectors.

In some embodiments, the vector backbone is selected to optimize host cell transformation efficiency and transgene expression. Many vectors capable of effectively transforming cells of a particular host insect, or group of host insects, and inducing expression of a transgene in the host have been identified and are known in the art.

In one aspect, provided herein are insects or nematodes transformed with a transgene vector described herein, and the progeny of the transformed insects or nematodes. In some embodiments, the transformed insect or nematode, or progeny thereof, overexpresses WalE1 relative to an insect or nematode harboring *Wolbachia* but that has not been transformed with the transgene vector. Because of the effects of WalE1 on *Wolbachia* replication and transmission, *Wolbachia*-harboring insects or nematodes overexpressing WalE1 will exhibit increased *Wolbachia* replication and transmission. In one embodiment, *Wolbachia*-infected *Drosophila melanogaster* transformed with an expression vector encoding WalE1 have a significantly increased *Wolbachia* titer in the presumptive oocyte and increased *Wolbachia* copy number in the next generation. In other embodiments, *Aedes albopictus, Aedes aegypti, Anopheles gamibiae, Anopheles stephansi, Culex pipiens, Culex tarsalis*, and *Culex quinquefasciatus*, and insects of the Culicidae and Drosophilidae families transformed with a transgene vector described herein are provided.

In some embodiments, overexpression of WalE1 is achieved by upregulating the endogenous gene's expression in a host infected with *Wolbachia*. In one embodiment, a CRISPR-on (clustered regularly interspaced short palindromic repeat) system is used to upregulate endogenous WalE1. The CRISPR-on system is a two-component transcriptional activator based on the CRISPR/Cas system comprising a nuclease-dead Cas9 (dCas9) protein fused with a transcriptional activation domain and a single guide RNA (sgRNA) with complementary sequence to a target gene promoter. The CRISPR-on system is described, for example, in International Patent Application publication WO/2014/172470 and in Yang H. et al., Cell Res., August 2013, which are hereby incorporated by reference in their entirety. To upregulate endogenous WalE1, sgRNA complementary to the WalE1-encoding polypeptide described above, or an associated expression control sequence, is fused with the dCas9 activator. The construct is then transformed into the target host. The WalE1-specific sgRNA sequence guides the dCas9 activator to the WalE1 gene, resulting in upregulation of endogenous WalE1 expression.

Also provided herein are methods for increasing *Wolbachia* replication and transmission in a host insect or nematode. In some embodiments, a target host is transformed with an expression vector described herein. Insect transformation methods are well known in the art, and commonly involve microinjection of developing insect embryos. In some embodiments, microinjection methods are selected to accommodate the physical and developmental characteristics of the target insects. Microinjection methods generally rely on the use of fine glass needles in conjunction with micromanipulators and a microscope. In some embodiments, a vector described herein is delivered via microinjection directly to insect germ cells. See O'Brochta and Atkinson, (2004) Transformation Systems in Insects, in Miller and Capy (Eds) *Mobile Genetic Elements* (pp. 227-254), Humana Press, Totowa, NJ.

Figure 6A:
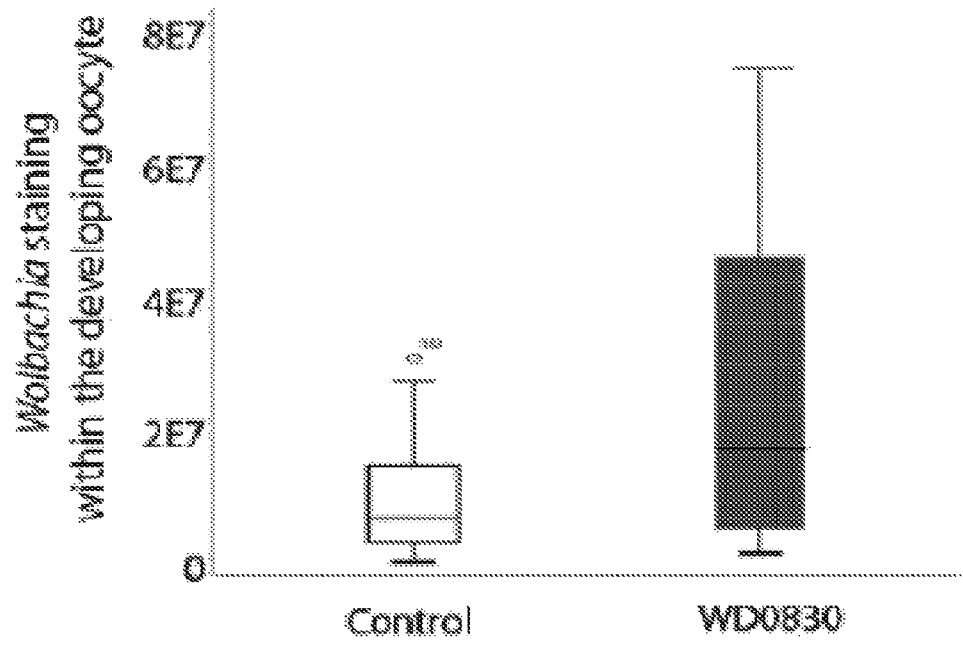
FIG. 6A is a bar graph indicating that the density of *Wolbachia* localizing to the developing oocyte is increased when WD0830 is expressed (as measured by EUB338 staining, see methods; N>=25 for each background; T-test: t=3.565; df=32.055; p=0.001).
Figure 6B:
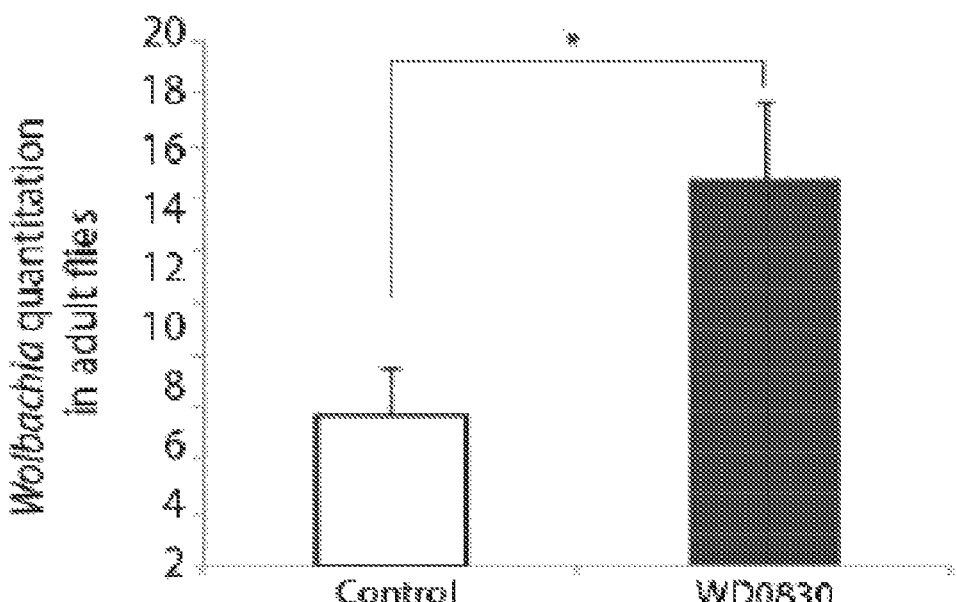
FIG. 6B is a bar graph indicating that *Wolbachia* density in whole transgenic animals is increased (assessed by qPCR (wsp/Rpl32)) relative to control animals (T-test: t=2.65; df=6; p=0.038).
Figures 6C, 6D:
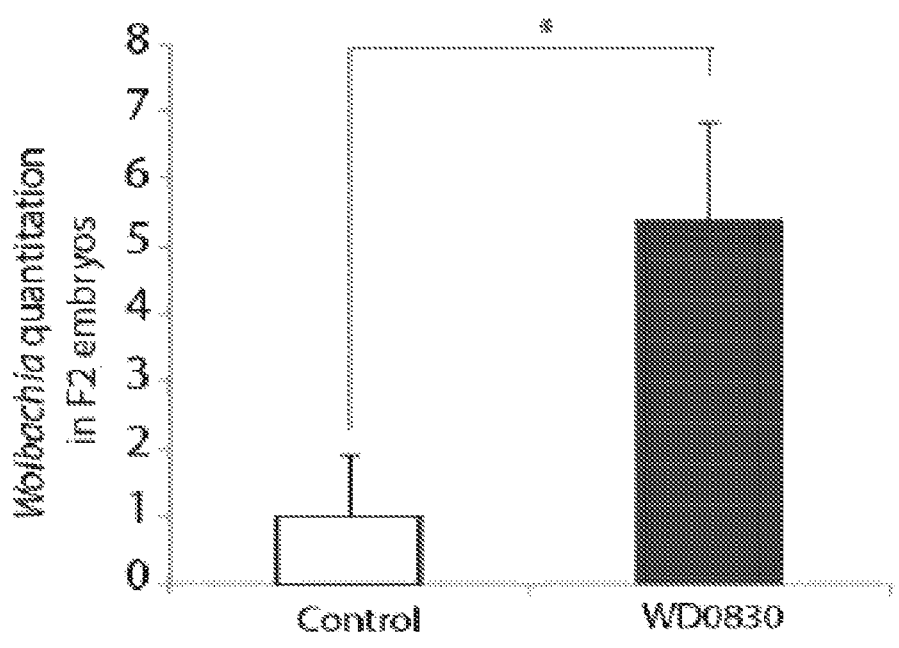
FIG. 6C is a bar graph indicating that 6 hour embryos from transgenic animals (F2) have greater *Wolbachia* loads (assessed by qPCR) compared to genetic control (fold difference in wsp/Rpl32=3.4–16.8; T-test: t=2.530; df=12.362; p=0.026).
FIG. 6D depicts the amount of F-actin staining (based on fluorescent-phalloidin binding) in ring canals adjacent to developing oocytes is altered upon RFP-WD0830 expression. Representative actin ring canals in transgenic flies expressing WD0830 (w-; osk-GAL4/+; P{UASp-RFP.WalE1}6M/+) compared to genetic controls (w-; osk-GAL4/+; +).

When the target host is infected with *Wolbachia*, this will result in overexpression of WalE1, or a functional fragment thereof. As described in the Examples and depicted in FIGS. 6A-C, the overexpression of WalE1 results in increased *Wolbachia* density in developing *D. melanogaster* oocytes (FIG. 6A) and adult transgenic flies (FIG. 6B) relative to controls. Progeny have greater *Wolbachia* loads compared to genetic controls (FIG. 6C). Controls, or control insects, as the term is used herein, are insects harboring *Wolbachia* but have not been induced to overexpress WalE1.

In some embodiments, the target host to be transformed is already infected by *Wolbachia*. In other embodiments, *Wolbachia* is introduced to the target host before, concurrently with, or after transformation with a vector described herein. One or more strains of *Wolbachia* can be introduced to the target host. Additional strains can be introduced to a target host that already harbors a particular *Wolbachia* strain. Strains that can be introduced to a target host include any *Wolbachia* strain, including for example wHa, wMel, wWil, wUni, wNo, wPip, wPel, wPela, wOv, wOo, wBm, wMel-Pop, wMelPop-CLA, wMelCS, wAu, wRi, wMau, and wCer2. By introducing the bacteria to host species that do not generally harbor *Wolbachia*, and supporting bacterial replication and transmission, new host species are capable of hosting large *Wolbachia* loads. This can be beneficial for both insect population control and insect host pathogen resistance as described herein.

Causing WalE1 overexpression in at least one insect host and releasing the WalE1 overexpressing host(s) into a general insect population can result in an increase in *Wolbachia* density and load throughout the general population over time. In some embodiments, the at least one insect host overexpressing WalE1 can be crossed at least once to produce a small population of transgenic insect hosts overexpressing WalE1. This small population can then be introduced into a larger general population.

In some embodiments, increased replication and transmission of *Wolbachia* results in control of an insect population. *Wolbachia* is known to induce reproductive effects in many insects, including cytoplasmic incompatibility, male-killing, and feminization. Further, *Wolbachia* has been demonstrated to reduce insect life-span in certain species. Thus, by increasing replication and transmission of *Wolbachia* in an insect population and causing or amplifying these effects, the population can be controlled.

In other embodiments, increased replication and transmission of *Wolbachia* in a host insect confers or improves pathogen resistance in the host insect. *Wolbachia* has been observed to protect insect hosts from RNA virus infection by inhibiting viral replication. This in turn can reduce virus transmission to humans. Pathogens to which resistance can be increased by the presence of *Wolbachia* include but are not limited to alphaviruses such as Chikungunya virus, Equine Encephalitis virus, and Western Equine Encephalitis virus; Flaviviruses such as dengue virus, West Nile virus, and Yellow Fever virus; Bunyaviruses such as La Crosse virus, Rift Valley fever virus, and Colorado tick fever virus; protozoans such as malaria parasites of the genus *Plasmodium*; and worms such as filarial nematodes. Reports have indicated that the pathogen-resistant effect of *Wolbachia* may be dependent on the particular strain (see, e.g., Hussain M. et al., J. Virol. 87(2):851-858, 2013 (epub Oct. 31, 2012)). In some embodiments, one or more specific strains of *Wolbachia* are introduced to a host insect transformed with a vector described herein in order to improve pathogen resistance in the host insect. The ability of particular *Wolbachia* strains to confer or improve pathogen resistance is known in the art Also provided herein are kits for use with the methods and expression vectors described herein. Expression vectors and/or host insects can be provided in the kit. The kits can also comprise a suitable container, an expression vector detailed herein, a live insect host, including insect embryos, and optionally one or more additional agents or materials, such as those supplies necessary for insect transformation, including needles and agents or media. In some embodiments the expression vector of the kit can be suitably aliquoted.

The container means of the kits will generally comprise at least one vial, test tube, flask, bottle, syringe or other container means, into which an expression vector may be placed.

EXAMPLES

The materials, methods, and embodiments described herein are further defined in the following Examples. Certain embodiments are defined in the Examples herein. It should be understood that these Examples, while indicating certain embodiments, are given by way of illustration only. From the disclosure herein and these Examples, one skilled in the art can ascertain the essential characteristics of this disclosure, and without departing from the spirit and scope thereof, can make various changes and modifications to the subject matter provided by this disclosure to adapt it to various usages and conditions.

Example I. wMel Protein WD0830 Elicits a Growth Defect in Yeast and Co-Localizes with Actin When expressed in the yeast *Saccharomyces cerevisiae*, bacterial effectors, but not housekeeping proteins, often result in growth inhibition due to conserved targeting of eukaryotic cellular processes. Thus, given the genetic intractability of *Wolbachia* and the lack of any in vitro assays to identify secreted proteins, the behavior of WD0830 was investigated when expressed in a yeast. The growth of yeast expressing a GFP WD0830 fusion protein was markedly suppressed as compared to expression of GFP alone, demonstrating the role of WD0830 as a secreted substrate (see FIG. 2A). This statistically significant growth-defect ($p < 0.0001$) was not observed in yeast that harbored clones encoding two other hypothetical *Wolbachia* proteins (see FIG. 2A; WD0041 or WD0462).

Given that effectors often exhibit similar subcellular localization patterns when expressed in yeast and mammalian cells, using fluorescence microscopy, the subcellular localization pattern of the GFP-WD0830-fusion protein was investigated when expressed in yeast. As depicted in FIG. 2B, GFP-WD0830 localized to filamentous structures within the yeast cell. This localization is reminiscent of actin filaments observed in wild type yeast expressing the *Salmonella typhimurium* type 3 secreted effector SipA, a protein that promotes bundling of actin filaments. The actin cytoskeleton of yeast that expresses GFP or GFP-WD0830 was stained with rhodamine-labelled phalloidin. As depicted in the GFP-only panel of FIG. 2B, the yeast actin cytoskeleton normally comprises cortical actin patches, and in polarized cells, actin filaments (which can be difficult to visualize). These structures were no longer observed in yeast that expressed GFP-WD0830. Rather, thick cables that co-localize with the labeled actin were observed, structures similar to those previously observed with expression of a *Salmonella* type 3 secreted effector, SipA, in yeast.

Methods

Amplification, Cloning and Transformation of wMel Genes

Genes from the wMel genome were amplified using modified forward primers to facilitate cloning using the Gateway pENTR-D/TOPO system and transformed into One Shot Top10 competent cells using standard protocols. Transformations were plated on selective plates and entry vector constructs generated by this reaction were sequence verified to confirm that protein products generated were in frame and correctly cloned. Correct entry vectors were used in combination with the pFus yeast destination vector in an LR clonase reaction and these resultant expression vectors were verified by restriction enzyme digests and sequencing. Yeast Molecular Biology, Quantitative Growth Assays and Microscopy Yeast strain S288C (BY4741 MATa) was transformed with sequence-verified expression vectors generated above using the PEG/Lithium acetate method. Yeast transformants were inoculated into selective synthetic media with 2% (w/v) glucose. These cultures were grown overnight to saturation (at 30° C.) before transfer into media containing 2% raffinose. After cultures reached an OD600 of 0.3-0.4 they were pinned into selective synthetic media containing 2% galactose (to induce expression) or 2% glucose (to repress). These growth assays were performed in triplicate. Optical densities of yeast growing in both conditions were measured using an Epoch plate reader at 24, 36, and 48 hours growth at 30° C.

Yeast harboring the expression vectors containing *Wolbachia* GFP-proteins were grown overnight in selective synthetic media containing 2% raffinose. Optical density measurements were taken and the yeast were diluted to an OD600 of 0.1 in synthetic media containing 2% galactose to induce expression. Localization of *Wolbachia* proteins was monitored in live yeast at 6 hrs and 24 hrs post-induction by live observation on a Nikon E800 fluorescent microscope with 40× oil objective and processed using Metamorph imaging software. To determine co-localization of the GFP-fusion protein with either actin or nuclei yeast were fixed in either 4% paraformaldehyde or Karnovsky fixative for 20 minutes at room temperature after a 6 hour induction and imaged using a 60× objective. Staining with rhodamine-labeled phalloidin to visualize the actin cytoskeleton was performed, and staining with DAPI (in mounting media) allowed for visualization of nuclei.

Yeast Protein Expression and Western Blots

Yeast harboring expression vectors containing proteins of interest were grown overnight in selective synthetic media containing 2% glucose. These cultures were diluted to an OD600 of 1.0 in synthetic media containing 4% galactose for 6, 16, or 24 hours before cells were harvested by centrifugation and frozen at −80° C. Frozen yeast pellets were disrupted using bead beating (Lysing matrix C on an MP FastPrep system, 20 s speed 6) in 750 μl of Lysis Buffer (150 mM NaCl, 1% Triton X-100, 50 mM Tris HCl, pH 8) supplemented with HALT Protease Inhibitor Cocktail and 5 mM EDTA. Lysates were centrifuged at 10,000×g for 1 min. at 4° C. to pellet cell debris and supernatants were used for subsequent Western blots.

Proteins were separated on 4-20% Tris-Glycine NB precast gels and transferred to PVDF membrane in Tris-Glycine transfer buffer with 15% methanol at 40 v on ice for 3-4 hours. The membrane was blocked for 5 minutes in Starting Block T20 (TBS) Blocking Buffer, followed by incubation in antibody (for 1 hour at RT or O/N at 4° C.). SuperSignal West Pico Chemiluminescent Substrate was used to detect HRP on immunoblots. Blots were re-probed after stripping in 100 μmM Glycine, 0.15 ND-40, 1% SDS, pH 2 for 1 hour at RT, then O/N at 4° C. PageRuler Prestained Protein Ladder was used as a molecular mass marker. Antibodies utilized include anti-actin at 1:1000; anti-GFP-HRP at 1:5000; and anti-PGK at 1:10,000.

Example II. WD0830 Interacts Directly with and Bundles F-Actin

To test whether *Wolbachia* protein directly binds to filamentous (F)-actin, it was determined whether WD0830 purified from *E. coli* directly bound purified actin filaments in a sedimentation assay. In this assay, proteins that bind to F-actin will co-sediment and thus pellet after ultracentrifugation. The ability of *E. coli*-purified WD0830 and alpha-actinin, a well-characterized actin binding protein, to directly interact with polymerized rabbit skeletal muscle actin was investigated and compared. As a negative control, bovine serum albumin (BSA) was included. In the co-sedimentation assay, proteins were incubated with polymerized actin and after subjecting the proteins to 150,000×g, both supernatants and pellets were separated by and visualized in a silver-stained SDS-PAGE gel. Proteins that directly interacted with actin were found in the pellet fraction only when actin was present. WD0830 and alpha-actinin both co-sedimented with actin (P fractions, FIG. 3A). The amount of *Wolbachia* protein WD0830 detected in the pellet was 24% (+10%, N=3) of the total when actin was present compared to 3% (+2%, N=3) without actin present (see FIG. 3A), which was consistent with direct binding. This enrichment was in the same range as observed for alpha-actinin, the positive control (28% in the pellet with actin compared to 4% in the pellet without actin). No sedimentation of BSA with actin was observed (see FIG. 3B). This result demonstrated that WD0830 directly interacts with actin.

Because GFP-WD0830 in yeast appeared to generate actin filaments similar to those generated by the *Salmonella* effector SipA, an actin bundling protein, the ability of WD0830 to bundle actin as assessed by a low speed sedimentation assay was compared. Strikingly, only in the presence of WD0830 did F-actin sediment at low speed (14K×g) (see FIG. 3B; LSP), consistent with bundling of actin by WD0830. The state of actin filaments was visualized after incubation with WD0830, with BSA, or without additional proteins, and was compared to incubation alone using fluorescence microscopy. In the presence of WD0830, but not BSA, F-actin bundles were observed (see FIG. 3C).

Methods

Actin Sedimentation and Bundling Assays

WD0830 was heterologously expressed in *E. coli* and centrifuged at high speed (150,000×g) for 1 hour at 4° C. before use. The supernatant was then used in actin sedimentation assays with purified rabbit skeletal actin. Actin was stored in G buffer before use (5 mM Tris-HCL pH 8.0 and 0.2 mM CaCl2), 0.2 mM ATP and 0.5 mM DTT). Polymerization was induced by the addition of 50 mM KCl, 2 mM MgCl2 and 1 mM ATP (final concentrations). The total amount of actin used in each assay was kept constant (40 µl of a 1 mg/mL stock added to each reaction). Either WD0830 (at 40 ng/mL final concentration), the actin binding protein alpha-actinin (used as a positive control for F-actin binding and sedimentation), BSA, or nothing additional (negative controls) was added to individual actin samples. These were first centrifuged at 14,000×g for 1 hour at 24° C. (to identify actin bundling activity) and then centrifuged at 150,000×g for 1.5 hr at 24° C. (to identify actin binding). Laemmli buffer was added to the supernatants and pellets resulting from this centrifugation and these samples were run on an SDS-PAGE gel to visualize the proteins using silver stain. The gel lanes were scanned and densitometry measured using ImageJ software. To image actin filaments, F-actin was prepared as above and before centrifugation, stained with Acti-stain 555 fluorescent phalloidin.

Figure 4:
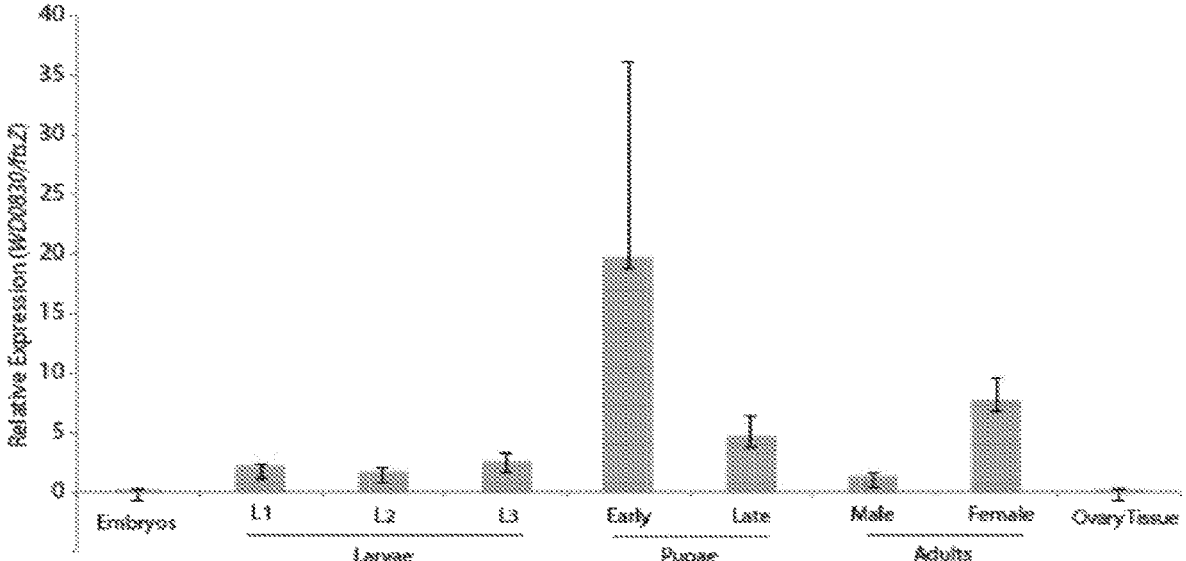
FIG. 4 is a bar graph illustrating expression of WD0830 (WalE1) during fly development. Depicted is qRT-PCR analysis of *Wolbachia*-infected flies at noted stages of development (each developmental stage represented by 5 biological replicates). WD0830 (WalE1) expression is presented relative to *Wolbachia* FtsZ at each developmental stage.

Example III. Characterization of Native and Ectopic WD0830 Expression During *Drosophila* Development To determine the levels of WD0830 expression during a natural infection, RNA from *Wolbachia*-infected *Drosophila* was harvested at seven different time points during fly development: embryos, 1st-3rd instar, early and late pupae, and adults (male and female). WD0830 expression was quantified and normalized to the ftsZ gene using qRT-PCR. FtsZ is a core conserved bacterial protein involved in cell division, known to be highly expressed throughout host development, making it an appropriate reference for transcription rates relative to bacterial growth. Expression of WD0830 relative to ftsZ was up-regulated during pupation, the developmental period during which ovary development begins and larval prepupal ovaries differentiate into the well characterized adult structures, a critical time point during *Drosophila* development (see FIG. 4). Components of secretion systems, including the inv/spa genes encoding the type III machinery, have been demonstrated to be up-regulated during host pupal development in other facultative intracellular symbionts, although the genes encoding the machinery of the *Wolbachia* type IV components have also been observed to be constitutively expressed throughout the host life cycle. The data presented here indicate that WD0830, relative to bacterial cell division, was most highly expressed during pupal development, coincident with the development and maturation of important adult structures such as the reproductive system (p<0.05).

Figure 5A:
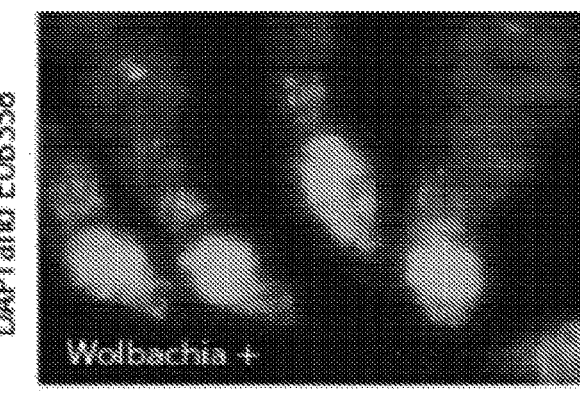
FIG. 5A presents two photographs that allow the comparison of fluorescent in situ hybridization probe EUB338 staining of *Wolbachia* in infected flies (stock #145) versus uninfected flies (stock #25211). Green signal is from EUB338-Alexa488 and blue signal is from host nuclei (DAPI stain).
Figure 5A:

WD0830 is expressed during a natural infection and during key time points (e.g., in the development of the reproductive organs). Because *Wolbachia* colonize the reproductive tract, and the actin cytoskeleton influences maternal transmission, it was determined whether the heterologous expression of WD0830 would affect the dynamics of a *Wolbachia* infection. *Drosophila* is an excellent model insect system in which to study a *Wolbachia* infection. The primary vertical colonization of flies by the bacteria occurs during oogenesis. Development of the oocyte begins in the anterior tip of the ovary, in a region called the germarium, a structure containing the germline stem cells from which oocytes differentiate. *Wolbachia* was observed throughout progressive stages of oocyte development within a single egg chamber and in the reproductive tissues (see FIG. 5A).

Figure 5B:
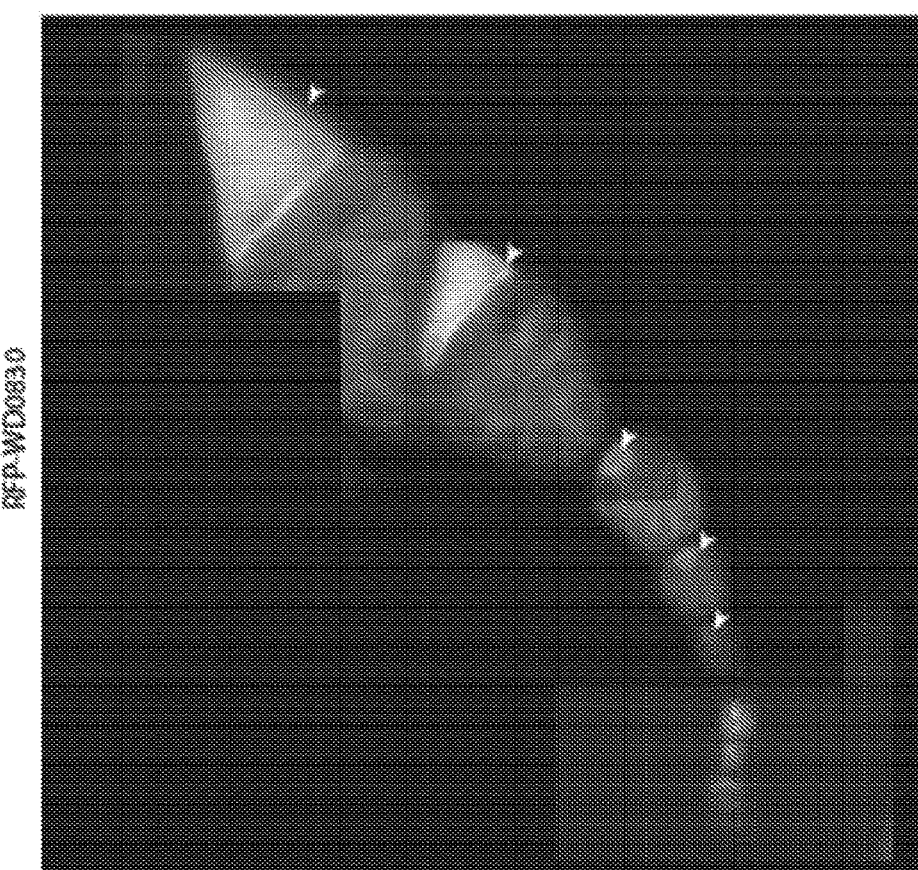
FIG. 5B presents a montage of four single-plane fluorescent microscopic images (raw images, unaltered) visualizing RFP-WD0830 in transgenic flies, expressed using the Osk- Gal4 driver. RFP-WD0830 localizes to the developing oocyte and maintains this localization during oogenesis (arrowheads).
Figure 5C:
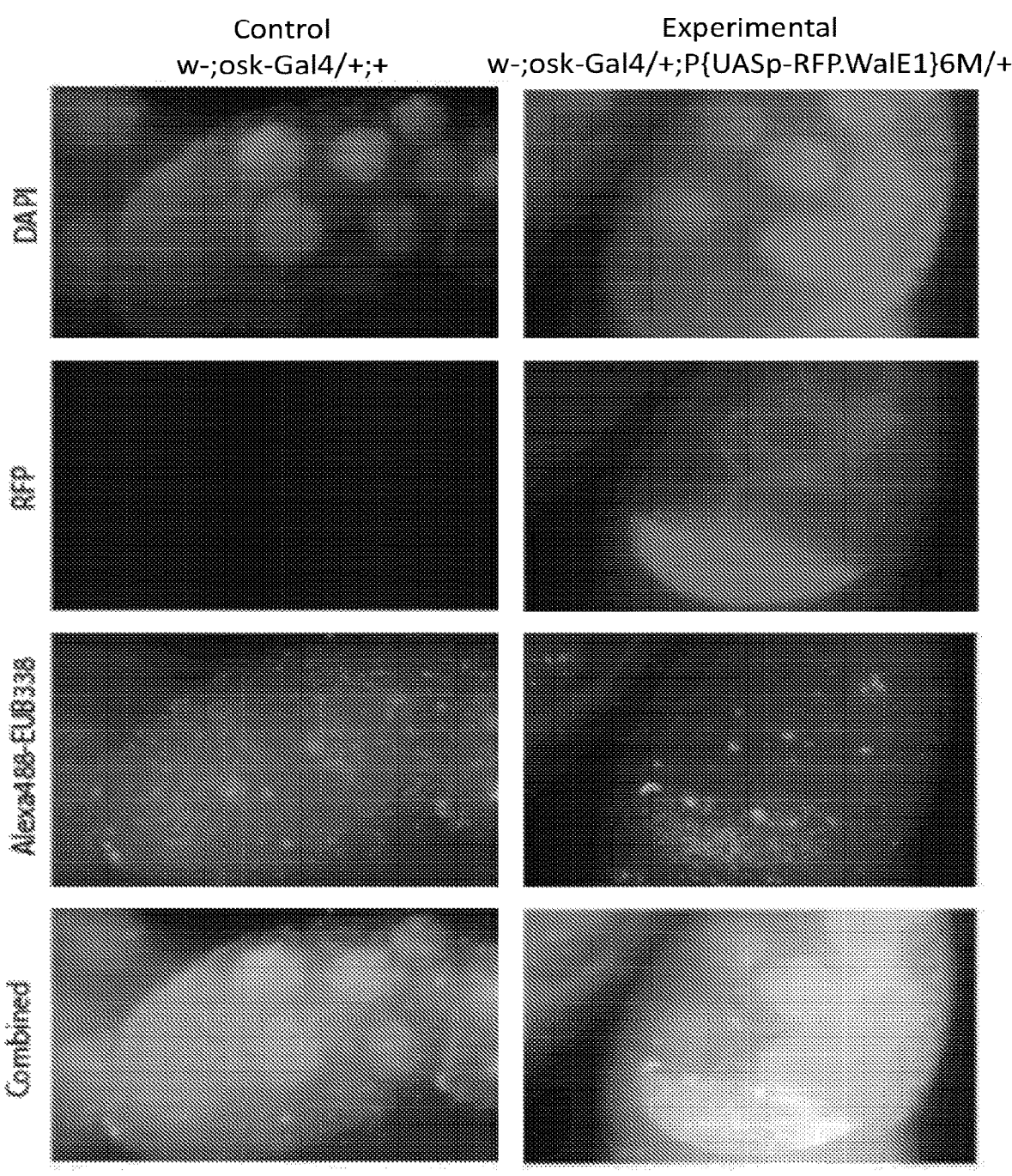
FIG. 5C presents a series of images depicting localization of *Wolbachia* and RFP-WD0830 in stage 9-10 oocytes in egg chambers from control (w-; osk-GAL4/+; +) animals, expressing GAL4 alone under the control of osk or experimental (w-; osk-GAL4/+; P{UASp-RFP.WALE1}6M/+) transgenic animals where RFP-WD0830 expression is driven under the control of osk-GAL4. These tissues were stained for chromosomal DNA (DAPI) and in situ probed for *Wolbachia* using EUB338.

RFP-WD0830 was overexpressed in *Wolbachia* infected transgenic flies using a variety of drivers (osk-GAL4, MTD-GAL4, matalpha4-GAL4). For each of these drivers, the same localization of the expressed protein was observed (see FIG. 5B; osk-GAL4, UAS-RFP-WD0830 presented as representative). RFP-WD0830 localized to the developing oocyte early and maintained this localization throughout oogenesis (see FIG. 5B). Expression of WD0830 in transgenic flies did not result in gross differences in fly fecundity; number of progeny between osk-GAL4; RFP-WD0830 flies and genetic controls did not significantly differ; t=1.486; df=17.076, p=0.155). In addition, density of *Wolbachia* in the developing oocyte was quantified using fluorescence in situ hybridization (see FIG. 5A), and no significant differences in *Wolbachia* density were observed in entire stage 9-10 egg chambers between control and transgenic flies (N>=25 for each background; p>0.05). However, the density of *Wolbachia* found within the developing oocyte was statistically significantly increased in RFP-WD0830-expressing flies compared to genetic controls (N>=25 for each background; T-test: t=3.565; df=32.055; p=0.001; see FIG. 5C and FIG. 6A). This higher titer infection was also observed utilizing qPCR on whole transgenic female flies over-expressing WD0830 compared to control flies (wsp/rpl32; t=2.65; df=6; p=0.038; see FIG. 6B).

Because the localization of WD0830 correlated with increased *Wolbachia* staining in developing oocytes, it was determined whether embryos derived from transgenic females overexpressing WD0830 would harbor higher *Wolbachia* titers. Using qPCR (wsp/Rpl32) on 6 hour embryos, it was determined that when transgenic flies express WD0830, their embryos harbor a greater quantity of *Wolbachia* than seen in genetic controls (with an increase between 3.4-16.8 for comparisons between embryos from three independent, transgenic lines expressing WD0830 and F1 embryos from control crosses, see FIG. 6C). Therefore, ectopic expression of WD0830 in an infected *Drosophila melanogaster* germ line increased the *Wolbachia* titer in the presumptive oocyte and increases the copy numbers of *Wolbachia* detected in the next generation (as demonstrated via qPCR).

Figure 6E:
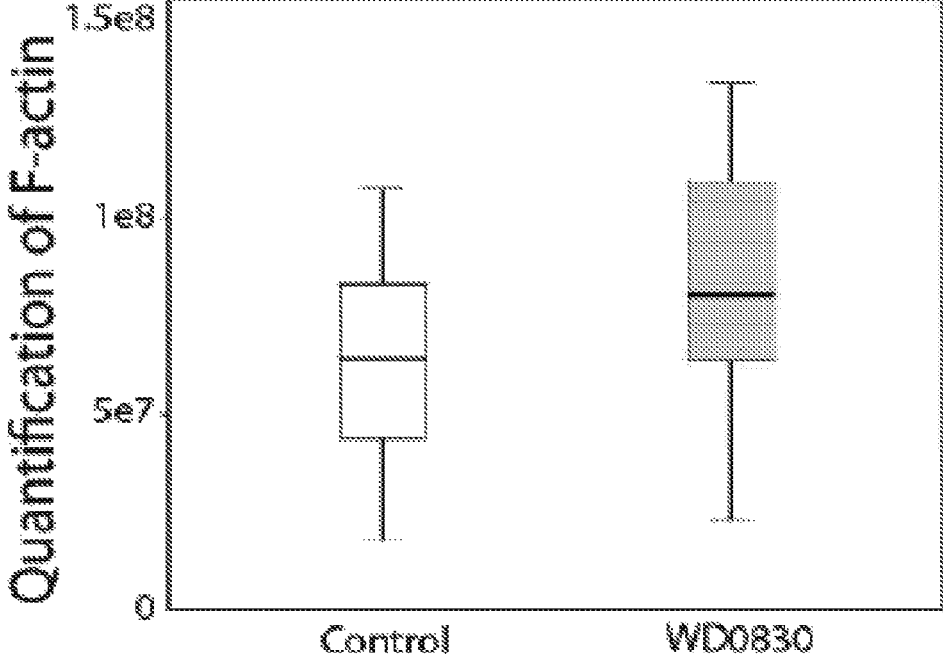
FIG. 6E is a bar graph indicating that expression of RFP-WD0830 increases the staining associated with actin ring canals adjacent to the developing oocyte (N>24 for each genotype; t=2.8314; df=47; p=0.006).

Overexpression of WD0830 in yeast corresponded to a change in the organization of the cortical F-actin cytoskeleton. Therefore, changes in the F-actin skeleton in transgenic flies were characterized. Nurse cells transfer their cytoplasmic contents through F-actin derived structures termed "ring canals," into the developing oocyte. This process is called "cytoplasmic dumping" and *Wolbachia* are thought to be delivered to the oocyte via this same route. Changes to the amount of F-actin associated with ring canals were investigated (based on fluorescent-phalloidin staining) when RFP-WD0830 is overexpressed. RFP-WD0830 accumulation in the cytoplasm of the developing oocyte was observed (see FIG. 5B) and in early egg chambers (stages 5-9), RFP-WD0830 expression resulted in thicker actin ring canals adjacent to the developing oocyte (see FIG. 6D). Overall, expression of RFP-WD0830 results in a 30% increase in the amount of F-actin staining in ring canals adjacent to the oocyte (N>24 for each genotype; t=2.8314; df=47; p=0.006; see FIG. 6E). Regardless of the stage examined, RFP-WD0830-expressing flies exhibited more fluorescent-phalloidin staining in actin ring canals compared to genetic controls (with a maximal 2 fold observed increase of in stage 5-6 oocytes).

WalE1 is the first *Wolbachia* protein identified to bind to and modify actin in vitro and alter infection dynamics in vivo. walE1 expression is upregulated during critical stages of host development and WalE1 transgenic flies produce oocytes and embryos with larger quantities of *Wolbachia*.

Methods

*Drosophila* Immunohistochemistry and Microscopy

Ovaries for immunolocalization were dissected in PBS solution 4 days after fly eclosion. Published protocols for fluorescent in situ hybridization were used (Toomey M. F., et al. (2013) PNAS, 110:10788-10793), with the following modifications: post-fixation in 4% paraformaldehyde in DEPC treated PBS; ovaries were dehydrated in methanol and stored overnight at −20° C. In the morning, washes in DEPC-PBST preceded a 5 minute proteinase K treatment (0.05 mg/mL) at 37° C. before incubation in hybridization buffer (50% formamide, 5×SSC, 250 mg/L SS DNA, 0.5× Denhardts, 20 mM Tris-HCl and 0.1% SDS). Universal bacterial probe EUB338 conjugated to Alexa488 was used to detect *Wolbachia* in the ovarioles. Rhodamine-labelled Phalloidin or Acti-stain 488 Fluorescent Phalloidin was used for F-actin detection, depending on the cross and the wavelengths utilized. Hybridized ovaries were mounted in Slow Fade "Gold"+DAPI antifade reagent.

Images were taken as Z-series stacks at 1.5 um intervals using a Nikon E800 fluorescent microscope with 40× oil objective and processed using Metamorph imaging software (Molecular Devices). Care was taken such that exposure times were normalized across all experiments. For quantification of both *Wolbachia* within the developing oocyte and actin ring canal staining intensity, maximum projections from stacks generated were used, excluding the peritoneal sheath. The irregular blob tool was used to outline the entire oocyte, using DAPI staining as a guide. For quantification of actin ring canal intensity, the oval tool base used to outline ring canals adjacent to the developing oocyte.

Transgenic *Drosophila* Stocks and Staging of Flies

Codon optimized WD0830 constructs were generated using the Gateway pENTR-D/TOPO system and transformed into One Shot Top10 competent cells. Correct entry vectors were used in combination with the pPRW destination vector (*Drosophila* Genomics Resource Center, plasmid stock #1137, features Gateway cassette, UASp promoter, N-terminal mRFP, and mini-white (complement)) in an LR clonase reaction and these resultant expression vectors were verified by restriction enzyme digests and sequencing. These constructs result in an N-terminal mRFP tag for WD0830. The purified plasmids were injected into *Drosophila* embryos. Thirteen independent lines on the X, second and third chromosomes were recovered. Standard methods were used for all crosses and culturing. *Drosophila* stocks were obtained from the Bloomington *Drosophila* Stock Center (BDSC) (flystocks.bio.indiana.edu/). Stock number 145, which carries w1, was used as the *Wolbachia*-infected control line used in characterization of WD0830 expression over development. The three *Wolbachia*-containing Gal4-driver stocks from BDSC used were as follows: "Oskar Driver," w[1118]; P All/CyO (BDSC #44241); "Maternal Triple Driver, (MTD)," P{w[+mC]=otu-GAL4::VP16.R}1, w[*]; P{w[+mC]=GAL4-nos.NGT}40; P{w[+mC]=GAL4:: VP16-nos.UTR}CG6325[MVD1] (BDSC #31777); and "Maternal Alpha Tubulin 67C driver," w[*]; P{w[+mC]=matalpha4-GAL-VP16}V37 (BDSC #7063).

Thirteen insertions stocks carrying pPRW-WD0830 on the X, 2 or 3rd chromosomes were created in a w[1118], *Wolbachia*-positive background and named P{w[+mC]=UASp-RFP.WalE1} (BestGene, Inc., Chino Hills, CA, USA). Homozygous viable insertions P{w[+mC]=UASp-RFP.WalE1}2M (Ch 2), 4M (Ch 3), 6M (Ch 3) and 7M (Ch3) were examined most extensively. Oskar-GAL4 driver and P{w[+mC]=UASp-RFP.WalE1}6M stocks were crossed for quantification of actin, *Wolbachia*, and localization of RFP-WD0830. *Wolbachia* infection status for stocks acquired from the BDSC and from BestGene, Inc. was determined via PCR.

Nucleic Acid Extractions and Quantitative PCR

To identify *Wolbachia* titer within embryos from mothers expressing WalE1, individual embryos were homogenized in 10 µL of water and this lysate was diluted 1:100 for quantitative PCR. Additionally, pools of 20-30 embryos were subjected to DNA extraction, and nucleic acids were diluted to <20 ng total for qPCR. Quantitative PCR was performed on this DNA to detect the *Wolbachia* titer (with reference to the host) using a StepOne Real-time PCR system and SybrGreen chemistry. wsp primers were used for *Wolbachia* (Forward: CATTGGTGTTGGTGTTGGTG (SEQ ID NO: 15); Reverse: ACCGAAATAACGAGCTCCAG (SEQ ID NO: 16)), and Rp132 primers for the host (Forward: CCGCTT-CAAGGGACAGTATC (SEQ ID NO: 17); Reverse: CAATCTCCTTGCGCTTCTTG (SEQ ID NO: 18)), with the following protocol: 95° C. for 10 min, then 40 cycles of 95° C. for 15 seconds and 60° C. for 1 minute. To characterize WalE1 expression throughout fly development, RNA and DNA were extracted from individual flies (stock 145) at different stages of development using a modified Trizol extraction protocol in which 500 µL of Trizol was added to flies and samples homogenized using a pestle. After a 5 minute incubation at room temperature, a 12,000 rcf centrifugation (at 4° C. for 10 min) was followed by a chloroform extraction. Aqueous phase containing RNA was extracted a second time with phenol:chloroform before isopropanol precipitation of RNA. This RNA pellet was washed and resuspended in The RNA Storage Solution. DNA extraction from the same flies was performed using ethanol precipitation of the organic phase during the first chloroform extraction. To detect the number of WalE1 transcripts, the RNA extracted from these flies was used. The SensiFAST SYBER Hi-ROX One-step RT mix and the StepOne Real-time PCR system was used on this RNA with the following primer set: WalE1F: TGG-GAAGAAAAGGCTCTGAA (SEQ ID NO: 19), WalE1R: TCAATGAGGCGCTTCTAGGT (SEQ ID NO: 20). As a reference for transcription activity of the core *Wolbachia* genome, the *Wolbachia* FtsZ gene was used (Forward: TTTTGTTGTCGCAAATACCG (SEQ ID NO: 21); Reverse:CCATTCCTGCTGTGATGAAA (SEQ ID NO: 22)). The wsp qPCR primer sets were not employed, as wsp's function is unclear and it is not known if wsp is stably expressed during development or in different tissues. Primers were designed to FtsZ because as a core protein involved in cell division, the quantities of FtsZ would better correlate with bacterial numbers and activity. Reactions were performed in duplicate or triplicate in a 96-well plate and calibration standards used to calculate primer efficiencies. These efficiencies, along with the CT values generated by the machine, were used to calculate the relative amounts of *Wolbachia* using the AA Ct (Livak) and Pfaffl methods.

The Examples discussed above are provided for purposes of illustration and are not intended to be limiting. Still other embodiments and modifications are also contemplated.

While a number of exemplary aspects and embodiments have been discussed above, those of skill in the art will recognize certain possible modifications, permutations, additions and sub combinations thereof. It is therefore intended that the following appended claims and claims hereafter introduced are to be interpreted to include all such modifications, permutations, additions and sub-combinations as are within their true spirit and scope.

What is claimed is:

1. A method to control a native mosquito population, the method comprising the steps of:

a) generating a population of transgenic *Wolbachia*-infected mosquitos, wherein the mosquitos are transformed with a vector comprising a polynucleotide that encodes *Wolbachia* actin localizing effector 1 (WalE1) or a functional fragment of Wal E1 operably linked to an expression control sequence and wherein the overexpression of WalE1 is greater than a mosquito harboring *Wolbachia* but lacking the vector comprising the polynucleotide that encodes *Wolbachia* actin localizing effector 1 (WalE1) or the functional fragment of WalE1 operably linked to the expression control sequence;

b) crossing the transgenic *Wolbachia*-infected female mosquitos with male mosquitos of a native mosquito population, wherein the *Wolbachia*-infected female mosquitos (i) are from the population of transgenic *Wolbachia*-infected mosquitos that overexpress (WalE1) polypeptide, or (ii) are progeny of the population of transgenic *Wolbachia*-infected male mosquitos that overexpress the WalE1 polypeptide;

c) generating a progeny mosquito population from the cross, wherein the progeny are capable of greater *Wolbachia* loads compared to a female mosquito of the native mosquito population; and d) releasing the *Wolbachia*-infected male progeny mosquitos to mate with *Wolbachia*-uninfected female mosquitos in the native mosquito population, thereby producing unviable progeny and controlling the native mosquito population.

2. A method according to claim 1, where the WalE1 polypeptide has an amino acid sequence that is at least 90% identical to the amino acid sequence of wMel WalE1 protein (SEQ ID NO: 2).

3. A method according to claim 1, where the WalE1 polypeptide has an amino acid sequence that is SEQ ID NO: 2.

4. A method according to claim 1, where the native mosquito population comprises mosquitos belonging to the family Culicidae.

5. A method according to claim 1, where the native mosquito population comprises mosquitos belonging to a genus selected from the group consisting of *Anopheles, Aedes,* and *Culex.*

6. A method according to claim 1, where the *Wolbachia*-injected male mosquitos are infected with one or more strains of *Wolbachia pipientis.*

7. A method according to claim 1, where the expression control sequence is expressible in an insect.

8. A method according to claim 1, wherein the mosquitos transformed are already infected by *Wolbachia.*

9. A method according to claim 1, wherein steps b) and c) are repeated one ore more times prior to the releasing step d).

10. A method of generating a mosquito population capable of greater *Wolbachia* infection loads, the method comprising the steps of:

a) generating a population of transgenic *Wolbachia*-infected mosquitos, wherein the mosquitos are transformed with a vector comprising a polynucleotide that encodes *Wolbachia* actin localizing effector 1 (WalE1) or a functional fragment of Wal E1 operably linked to an expression control sequence and wherein the overexpression of WalE1 is greater than a mosquito harboring *Wolbachia* but lacking the vector comprising the polynucleotide that encodes *Wolbachia* actin localizing effector 1 (WalE1) or the functional fragment of Wal E1 operably linked to the expression control sequence;

b) crossing the transgenic *Wolbachia*-infected male mosquitos with a female mosquito of a native mosquito population, wherein the *Wolbachia*-infected male mosquitos (i) are from the population of transgenic *Wolbachia*-infected mosquitos that overexpress (WalE1) polypeptide, or (ii) are progeny of the population of transgenic *Wolbachia*-infected male mosquitos that overexpress the WalE1 polypeptide;

c) generating a progeny mosquito population from the cross, wherein the progeny are capable of greater *Wolbachia* loads compared to a female mosquito of the native mosquito population.

* * * * *

SEQUENCE LISTING

```
<160> NUMBER OF SEQ ID NOS: 22

<210> SEQ ID NO 1
<211> LENGTH: 1347
<212> TYPE: DNA
<213> ORGANISM: Wolbachia pipientis

<400> SEQUENCE: 1
atgaaacaag gagataagat tcttgtagta agtacagcaa gtggattatt tacggcagta      60
ctaccacttt tggcagttgg tgcaacactt gctataccgg gtgctatagt tggtcttgct     120
ttatatttcg ctgtaaaagt cgctgtaaaa gcagttcaat ctggatataa agggctcaag     180
tggtcagcag aaaaaacagt tgatggggcg aaatatactg ctgggaaagt taaggacgca     240
tcaacatacg ctgccggaaa agttagagat ggtgctatgc atgttaaaga taaggtgaaa     300
gaaggttatg aacattcagt agattcactg aaaaaaggcg ctagttttgt aggcgaagga     360
gtggcaaata agttccataa ggcatctggt gagacggact atttagataa ggtaaaaagg     420
tttactccag atgcaattaa gaaatctgac gaaataagaa atgatatgaa agcaattttt     480
gctgataaag gaaataattc tgggttagtg aaaaatatac tttctggaat atcgtcagaa     540
attgatttaa aaatggcaga gaaggcaaaa tcaggggaga ttgaacatac ttctggatgg     600
caagtacaga aagaattcat taataattta aatgaaaaaa gcttgcataa cttgttaaca     660
caaaggtcat tacctaaagg tagttatttc atcgacagtg ttttctctga acatcacgat     720
gaaattaaga aggttattaa agaatgtaga gaaaatcatt tgtactcaag cgtaagcaat     780
atgtttgaca gagcagagaa aaaagctaac aggccttctg tcaaaagttt aactaggtct     840
gtgtcatcat cattctcttc actgggaaga aaaggctctg aacaatctaa cagcttgtca     900
aaaagcaatt cactaaattc tataggaact gaaagtactg ctactgtctc tgattcagat     960
tctcagaact ttgcaacagt ccgtagaagc aattcatcta gtagcttaac tcctaagctt    1020
actccagttg ctccaccaga actacctaga agcgcctcat tgactaactt aaatggacaa    1080
agttctttca gtgaagatgt tctcagtgat cctattgtgg agcaaaacct ggatagtttg    1140
agtaacagaa ctctcactca cagtaattct actgatagtg gaatgggttc tggttcttct    1200
acgctaacaa gaaaacaagt tcttccttta aaagaagaat ttgacagaga actcgaagaa    1260
aagttggcaa aacgactcgc atctctagat caacctagtg cagaacctgt caactcaaga    1320
gctacagcaa ctccaggaac agtgtaa                                        1347

<210> SEQ ID NO 2
<211> LENGTH: 448
<212> TYPE: PRT
<213> ORGANISM: Wolbachia pipientis

<400> SEQUENCE: 2

Met Lys Gln Gly Asp Lys Ile Leu Val Val Ser Thr Ala Ser Gly Leu
1               5                   10                  15

Phe Thr Ala Val Leu Pro Leu Leu Ala Val Gly Ala Thr Leu Ala Ile
```

-continued

```
              20                  25                  30
Pro Gly Ala Ile Val Gly Leu Ala Leu Tyr Phe Ala Val Lys Val Ala
         35                  40                  45

Val Lys Ala Val Gln Ser Gly Tyr Lys Gly Leu Lys Trp Ser Ala Glu
         50                  55                  60

Lys Thr Val Asp Gly Ala Lys Tyr Thr Ala Gly Lys Val Lys Asp Ala
65                  70                  75                  80

Ser Thr Tyr Ala Ala Gly Lys Val Arg Asp Gly Ala Met His Val Lys
                   85                  90                  95

Asp Lys Val Lys Glu Gly Tyr Glu His Ser Val Asp Ser Leu Lys Lys
                   100                 105                 110

Gly Ala Ser Phe Val Gly Glu Gly Val Ala Asn Lys Phe His Lys Ala
         115                 120                 125

Ser Gly Glu Thr Asp Tyr Leu Asp Lys Val Lys Arg Phe Thr Pro Asp
         130                 135                 140

Ala Ile Lys Lys Ser Asp Glu Ile Arg Asn Asp Met Lys Ala Ile Phe
145                 150                 155                 160

Ala Asp Lys Gly Asn Asn Ser Gly Leu Val Lys Asn Ile Leu Ser Gly
                   165                 170                 175

Ile Ser Ser Glu Ile Asp Leu Lys Met Ala Glu Lys Ala Lys Ser Gly
                   180                 185                 190

Glu Ile Glu His Thr Ser Gly Trp Gln Val Gln Lys Glu Phe Ile Asn
                   195                 200                 205

Asn Leu Asn Glu Lys Ser Leu His Asn Leu Leu Thr Gln Arg Ser Leu
         210                 215                 220

Pro Lys Gly Ser Tyr Phe Ile Asp Ser Val Phe Ser Glu His His Asp
225                 230                 235                 240

Glu Ile Lys Lys Val Ile Lys Glu Cys Arg Glu Asn His Leu Tyr Ser
                   245                 250                 255

Ser Val Ser Asn Met Phe Asp Arg Ala Glu Lys Lys Ala Asn Arg Pro
                   260                 265                 270

Ser Val Lys Ser Leu Thr Arg Ser Val Ser Ser Ser Phe Ser Ser Leu
                   275                 280                 285

Gly Arg Lys Gly Ser Glu Gln Ser Asn Ser Leu Ser Lys Ser Asn Ser
         290                 295                 300

Leu Asn Ser Ile Gly Thr Glu Ser Thr Ala Thr Val Ser Asp Ser Asp
305                 310                 315                 320

Ser Gln Asn Phe Ala Thr Val Arg Arg Ser Asn Ser Ser Ser Ser Leu
                   325                 330                 335

Thr Pro Lys Leu Thr Pro Val Ala Pro Pro Glu Leu Pro Arg Ser Ala
                   340                 345                 350

Ser Leu Thr Asn Leu Asn Gly Gln Ser Ser Phe Ser Glu Asp Val Leu
                   355                 360                 365

Ser Asp Pro Ile Val Glu Gln Asn Leu Asp Ser Leu Ser Asn Arg Thr
         370                 375                 380

Leu Thr His Ser Asn Ser Thr Asp Ser Gly Met Gly Ser Gly Ser Ser
385                 390                 395                 400

Thr Leu Thr Arg Lys Gln Val Leu Pro Leu Lys Glu Glu Phe Asp Arg
                   405                 410                 415

Glu Leu Glu Glu Lys Leu Ala Lys Arg Leu Ala Ser Leu Asp Gln Pro
                   420                 425                 430

Ser Ala Glu Pro Val Asn Ser Arg Ala Thr Ala Thr Pro Gly Thr Val
         435                 440                 445
```

-continued

```
<210> SEQ ID NO 3
<211> LENGTH: 45
<212> TYPE: PRT
<213> ORGANISM: Wolbachia pipientis

<400> SEQUENCE: 3

Lys Gly Leu Lys Trp Ser Ala Glu Lys Thr Val Asp Gly Ala Lys Tyr
1               5                   10                  15

Thr Ala Gly Lys Val Lys Asp Ala Ser Thr Tyr Ala Ala Gly Lys Val
            20                  25                  30

Arg Asp Gly Ala Val His Val Lys Asp Lys Val Lys Glu
        35                  40                  45

<210> SEQ ID NO 4
<211> LENGTH: 55
<212> TYPE: PRT
<213> ORGANISM: Wolbachia pipientis

<400> SEQUENCE: 4

Val Ala Val Lys Ala Val Gln Ser Gly Tyr Lys Gly Leu Lys Trp Ser
1               5                   10                  15

Ala Glu Lys Thr Val Asp Gly Ala Lys Tyr Thr Ala Gly Lys Val Lys
            20                  25                  30

Asp Ala Ser Thr Tyr Ala Ala Gly Lys Val Arg Asp Gly Ala Met His
        35                  40                  45

Val Lys Asp Lys Val Lys Glu
    50                  55

<210> SEQ ID NO 5
<211> LENGTH: 55
<212> TYPE: PRT
<213> ORGANISM: Wolbachia pipientis

<400> SEQUENCE: 5

Val Ala Val Lys Ala Val Gln Ser Gly Tyr Lys Gly Leu Lys Trp Ser
1               5                   10                  15

Ala Glu Lys Thr Val Asp Gly Ala Lys Tyr Thr Ala Gly Lys Val Lys
            20                  25                  30

Asp Ala Ser Thr Tyr Ala Ala Gly Lys Val Arg Asp Gly Ala Met His
        35                  40                  45

Val Lys Asp Lys Val Lys Glu
    50                  55

<210> SEQ ID NO 6
<211> LENGTH: 55
<212> TYPE: PRT
<213> ORGANISM: Wolbachia pipientis

<400> SEQUENCE: 6

Val Ala Val Lys Ala Val Gln Ser Gly Tyr Lys Gly Leu Lys Trp Ser
1               5                   10                  15

Ala Glu Lys Thr Val Asp Gly Ala Lys Tyr Thr Ala Gly Lys Val Lys
            20                  25                  30

Asp Ala Ser Thr Tyr Ala Ala Arg Lys Val Arg Asp Gly Ala Met His
        35                  40                  45

Val Lys Asp Lys Val Lys Glu
    50                  55
```

```
<210> SEQ ID NO 7
<211> LENGTH: 57
<212> TYPE: PRT
<213> ORGANISM: Wolbachia pipientis

<400> SEQUENCE: 7

Val Ala Val Lys Ala Val Gln Ser Gly Tyr Lys Gly Leu Lys Trp Ser
1               5                   10                  15

Ala Glu Lys Thr Val Glu Gly Ala Lys His Ile Gly Gly Lys Ile Lys
            20                  25                  30

Asp Gly Tyr Glu Tyr Ser Ala Asp Ser Leu Lys Arg Gly Ala Ser Phe
        35                  40                  45

Val Ser Glu Lys Thr Lys Glu Lys Thr
    50                  55

<210> SEQ ID NO 8
<211> LENGTH: 47
<212> TYPE: PRT
<213> ORGANISM: Wolbachia pipientis

<400> SEQUENCE: 8

Lys Gly Leu Lys Trp Ser Ala Glu Lys Thr Val Glu Gly Ala Lys His
1               5                   10                  15

Ile Gly Gly Lys Ile Lys Asp Gly Ala Val Tyr Ala Lys Asn Ser Val
            20                  25                  30

Lys Glu Thr Ala Ser Ser Val Lys Gln Ala Thr Gln Glu Arg Ala
        35                  40                  45

<210> SEQ ID NO 9
<211> LENGTH: 47
<212> TYPE: PRT
<213> ORGANISM: Wolbachia pipientis

<400> SEQUENCE: 9

Lys Gly Leu Lys Trp Ser Ala Glu Lys Thr Val Glu Gly Ala Lys His
1               5                   10                  15

Ile Gly Gly Lys Ile Lys Asp Gly Ala Val Tyr Ala Lys Asn Ser Val
            20                  25                  30

Lys Glu Thr Ala Ser Ser Val Lys Gln Ala Thr Gln Glu Arg Ala
        35                  40                  45

<210> SEQ ID NO 10
<211> LENGTH: 42
<212> TYPE: PRT
<213> ORGANISM: Wolbachia pipientis

<400> SEQUENCE: 10

Val Lys Ala Val Gln Ser Gly Tyr Lys Gly Leu Lys Trp Ser Ala Glu
1               5                   10                  15

Lys Thr Val Glu Gly Ala Lys His Ile Gly Gly Lys Ile Lys Asp Gly
            20                  25                  30

Ala Val Tyr Ala Lys Asn Ser Val Lys Glu
        35                  40

<210> SEQ ID NO 11
<211> LENGTH: 63
<212> TYPE: PRT
<213> ORGANISM: Mus musculus

<400> SEQUENCE: 11

Met Asp Val Phe Met Lys Gly Leu Ser Lys Ala Lys Glu Gly Val Val
```

-continued

```
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Thr Thr Val Ala Glu Lys Thr Lys Glu Gln Val
    50                  55                  60
```

```
<210> SEQ ID NO 12
<211> LENGTH: 54
<212> TYPE: PRT
<213> ORGANISM: Wolbachia pipientis

<400> SEQUENCE: 12

Lys Ile Lys Asn Ser Phe Lys Tyr Ala Ala Asp Lys Thr Lys Asp Gly
1               5                   10                  15

Ala Val Cys Ala Lys Asp Ser Val Lys Glu Ala Val Ser Tyr Ile Gly
            20                  25                  30

Gln Ala Ala Arg Glu Glu Thr Ser Ser Ala Leu Lys Ile Ile Gly Asn
        35                  40                  45

Lys Met Asn Asn Phe Gly
    50
```

```
<210> SEQ ID NO 13
<211> LENGTH: 54
<212> TYPE: PRT
<213> ORGANISM: Wolbachia pipientis

<400> SEQUENCE: 13

Lys Ile Lys Asn Ser Phe Lys Tyr Ala Ala Asp Lys Thr Lys Asp Gly
1               5                   10                  15

Ala Val Cys Ala Lys Asp Ser Val Lys Glu Ala Val Ser Tyr Ile Gly
            20                  25                  30

Gln Ala Ala Arg Glu Glu Thr Ser Ser Ala Leu Lys Ile Ile Gly Asn
        35                  40                  45

Lys Met Asn Asn Phe Gly
    50
```

```
<210> SEQ ID NO 14
<211> LENGTH: 39
<212> TYPE: PRT
<213> ORGANISM: Wolbachia pipientis

<400> SEQUENCE: 14

Gly Phe Arg Tyr Ala Ala Glu Lys Thr Ile Lys Gly Val Lys Tyr Ile
1               5                   10                  15

Gly Glu Lys Ile Lys Asp Ser Ala Ile His Thr Lys Asp Ser Val Lys
            20                  25                  30

Glu Ala Val Ser Ser Ile Gly
        35
```

```
<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
cattggtgtt ggtgttggtg                                            20
```

-continued

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
accgaaataa cgagctccag                                            20

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
ccgcttcaag ggacagtatc                                            20

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
caatctcctt gcgcttcttg                                            20

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
tgggaagaaa aggctctgaa                                            20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
tcaatgaggc gcttctaggt                                            20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
ttttgttgtc gcaaataccg                                            20

<210> SEQ ID NO 22
<211> LENGTH: 20
<212> TYPE: DNA
<213> ORGANISM: Artificial Sequence
<220> FEATURE:

-continued

```
<223> OTHER INFORMATION: Synthetic primer

<400> SEQUENCE: 22
ccattcctgc tgtgatgaaa                                    20
```